United States Patent [19]

Heinz et al.

[11] Patent Number: 5,046,515

[45] Date of Patent: Sep. 10, 1991

[54] PERMANENT SHAPING AGENT FOR HUMAN HAIR AND THE METHOD FOR THE PERMANENT SHAPING OF HUMAN HAIR

[75] Inventors: Dieter Heinz, Gustavsburg; Siegfreid Kingeter, Dieburg; Burkhard Rose, Darmstadt-Eberstadt, all of Fed. Rep. of Germany; Hirotsugu Segawa, Osaka, Japan; Jürgen Tennigkeit, Seeheim, Fed. Rep. of Germany

[73] Assignee: Goldwell GmbH, Darmstadt-Eberstadt, Fed. Rep. of Germany

[21] Appl. No.: 54,143

[22] Filed: May 21, 1987

Related U.S. Application Data

[63] Continuation of Ser. No. 777,088, filed as PCT EP 84/00421 on Dec. 21, 1984, published as WO 85/02998 on Jul. 18, 1985, abandoned.

[30] Foreign Application Priority Data

Jan. 14, 1984 [DE] Fed. Rep. of Germany ....... 3401221

[51] Int. Cl.$^5$ .............................................. A45D 7/04
[52] U.S. Cl. .................................... 132/204; 132/205; 132/207
[58] Field of Search ....................... 132/204, 205, 207; 424/70-72

[56] References Cited

U.S. PATENT DOCUMENTS 2,719,813 10/1955 Haefele ............................... 132/7 X
2,794,440 6/1957 Levie ...................................... 132/7

OTHER PUBLICATIONS

Edward Sagarin, Cosmetics Science and Technology, 1957, pp. 572-576, 634-635.

Primary Examiner—V. Millin

[57] ABSTRACT

A permanent shaping agent for human hair.

The permanent shaping agent containing one or more hair keratin-reducing active substances is adjusted by means of stiffening additives to a consistency that is viscous to cream-like at room temperature with a viscosity of over 100 mPa x s.

The stiffening additives are selected such that the permanent shaping agent, upon warming to a temperature within a temperature range between 25° and 42° C, undergoes a decided loss of viscosity of over 60% with respect to the initial viscosity, to a value under 50 mPa x s, i.e., becomes fluid within this temperature range.

The permanent shaping agent of raised viscous or creamy consistency is applied to hair on curlers and then the viscosity of the permanent shaping agent is lowered, by elevating its temperature in situ, so that the liquified agent penetrates into the hair on the curlers.

6 Claims, No Drawings

PERMANENT SHAPING AGENT FOR HUMAN HAIR AND THE METHOD FOR THE PERMANENT SHAPING OF HUMAN HAIR

This application is a continuation of application Ser. No. 777,088 filed as PCT EP 84/00421 on Dec. 21, 1984, published as WO 85/02998 on Jul. 18, 1985, now abandoned.

The invention relates to a permanent shaping agent for human hair, having one or more active substances for reducing hair keratin which are adjusted with one or more stiffening additives to a viscous to creamy consistency, the permanent shaping agent at least greatly reducing dripping from the hair being treated, and it relates to a method for the permanent shaping of human hair by the use of the viscous to creamy permanent shaping agent.

For the permanent shaping of human hair, i.e., so-called "permanent waving," liquid permanent shaping agents are mostly used up to the present time, although agents in the form of creams or agents which are in the form of foam when applied have been proposed and used and are being used. In the use of the liquid permanent shaping agents, two different methods of use are generally practiced. The previously washed and toweled-dry hair is, as a rule, first divided into several portions, which are then premoistened with a portion of the liquid permanent shaping agent, and then wound on curlers. When the winding is completed, the curls are wetted with the remainder of the liquid permanent shaping agent. In the other method, the washed and toweled-dry hair is also divided into several portions and then wound onto curlers without first being moistened with the permanent shaping agent. The curled hair is then thoroughly wetted with all of the necessary amount of the permanent shaping agent. At the end of the required time of action of the hair shaping agent, the curled hair is rinsed with water and fixed with the aqueous solution of an oxidizing agent. Since when liquid permanent shaping agents are used the hair portions already treated do not differ in appearance from untreated hair portions, overdosing or underdosing of the permanent shaping agent in some of the hair portions, with the resultant disadvantages, is not impossible. In the former case insufficient shaping of the hair portions in question occurs, while in the latter case the liquid shaping agent can run down on the scalp and face of the person being treated, and can lead to skin irritation.

The invention is addressed, therefore, to the problem of devising a permanent shaping agent for human hair, which will have a reduced tendency to drip off or run down, and which will make possible, in a one-step process, a reliable shaping of the hair in a manner that is uniform from the hair line all the way to the more delicate ends of the hairs.

In accordance with the invention this problem is solved by the fact that the permanent shaping agent has an initial viscosity of at least 100 mPa/s and, upon warming to a temperature within a range between 25° and 42° C., undergoes a decided loss of viscosity of more than 60% to a value below 50 mPa/s, the viscosity measurement being performed with a Brookfield Rotation viscosimeter with a No. 3 spindle at 5 rpm.

The stiffening additive or additives can contain one or more paraffins, Vaseline, ceresins, fatty alcohols, fatty acids, waxes, polyglycols, polyglycol ester, polyglycol ether, aminoxides, lanolin derivatives and/or esters and ethers of monovalent or polyvalent organic acids with monovalent or polyvalent alcohols. These or other suitable viscosity-increasing additives, therefore, in mixture with the hair-keratin-reducing (known) active substance or active substances and, if desired, additional stabilizers, care substances and perfume oils, give a firm permanent shaping agent which can be applied with reduced tendency to drip down or run off, and which can then be liquefied by heat to such an extent that it penetrates even into the inner layers of the hair wound on hair curlers.

In the use of the permanent shaping agent, the hair, washed and toweled-dry in the usual manner, is wound in portions onto curlers, the procedure in accordance with the invention then being to apply the permanent shaping agent to the hair portions which have been wound or arranged without permanent shaping agent and are lying externally on the curlers, then to decrease the viscosity of the permanent shaping agent by raising the temperature to a range between 25° and 42° C. to such an extent that it becomes fluid and penetrates the curled hair portions and wets them through, and finally, after a sufficient time for the permanent shaping agent to act, to rinse the permanent shaping agent from the hair in a known manner and treat the hair as usual with a solution having an oxidizing action. On account of the viscous or creamy consistency it has when applied, the permanent shaping agent cannot drip down and run off and wet the scalp much less run into the face. Even though the permanent shaping agent becomes fluid when heated after application, it first penetrates into the inner hair portions in the curler and wets them. Only in the case of overdosing, which, however, is avoidable by using according to the directions, does excess permanent shaping agent then sink down into the scalp. In comparison with the conventional liquid permanent waves, the treatment is thus perceived to be substantially more comfortable. Another advantage of the permanent shaping agent which can be applied in the manner of the invention lies in the fact that, due to its stiffness, it is visible on the outside of the hair and therefore permits a uniform application to all parts of the hair without overdosing or underdosing, and thus also leads to a uniform waving.

If the permanent shaping agent is adjusted by the selection of appropriate additives such that the reduction of viscosity occurs at temperatures below about 30° C., the body heat of the person being treated suffices to raise the temperature of the permanent shaping agent, in which case it can be desirable to cover the curled hair after the application of the permanent shaping agent with a hood preventing heat losses. In this method of procedure, the lowering of the viscosity of the permanent shaping agent takes place relatively slowly, so that the soaking of the hair curls from the outside in is retarded. The time of action on the outer layers of the curls, i.e., at the hair line, is thus longer and thus the effect is greater, than it is on the more delicate ends of the hair.

If, however, the lowering of the viscosity of the permanent shaping agent begins at higher temperatures, the necessary temperature increase can be accomplished by means of radiant heating, e.g., by infrared radiators, or by blowing heated air against the hair, for example from the drying hood commonly used in hairdressing parlors.

The invention is further explained hereinbelow with the aid of four examples of its embodiment, for which the formulas are first given in the following list.

|  | Examples | | | |
| --- | --- | --- | --- | --- |
|  | 1 | 2 | 3 | 4 |
| Cetyl alcohol | — | — | 0.50 g | — |
| Myristyl alcohol | 0.80 g | 0.60 g | 0.40 g | 0.70 g |
| Oleyl alcohol 92–96 | 0.80 g | 0.60 g | — | 0.15 g |
| Paraffin oil (high fluidity) | — | — | — | 1.00 g |
| Vaseline | 1.00 g | 1.00 g | 1.00 g | — |
| PEG-40 hydr. castor oil | 1.00 g | 0.75 g | 0.75 g | 0.30 g |
| Ceteareth-25 | 0.50 g | 0.35 g | 0.50 g | 0.80 g |
| Perfume oil | 0.40 g | 0.40 g | 0.40 g | 0.40 g |
| Propylene glycol (1,3) | 1.50 g | 1.50 g | 1.50 g | 1.50 g |
| Cetyltrimethylammonium chloride | 0.10 g | 0.10 g | 0.10 g | 0.10 g |
| Alkyldimethylbetaine 30 | — | — | — | 1.00 g |
| Thioglycolic acid 80% | 12.50 g | 12.50 g | 12.50 g | 10.00 g |
| Ammonia 25% | 7.35 g | 7.35 g | 7.35 g | 7.50 g |
| Ammonium hydrogen carbonate | 4.00 g | 4.00 g | 4.00 g | 2.00 g |
| Water, demineralized, to make | 100 ml | 100 ml | 100 ml | 100 ml |

In the permanent shaping agents composed in accordance with the above formulas, the viscosity values (as measured with a Brookfield Rotation viscosimeter with No. 3 spindle at a speed of 5 rpm) were determined at different temperatures within the temperature range here involved.

EXAMPLE 1

At 20° C. a viscosity of 1350 mPa/s was measured, which at 30° C. dropped to 20 mPa/s and at 40° C dropped to less than 5 mPa/s. The fusion range of the permanent shaping agent was around 26° to 27° C., so that it is appropriate for the permanent-waving of normal hair without external application of heat.

EXAMPLE 2

In this example a viscosity of 710 mPa/s was measured at 20° C., which dropped to 10 mPa/s at 30° C. and to less than 5 mPa/s at 40° C. In this case, too, the fusion range of 25° to 27° is so low that the substance is suitable for use without the external application of heat.

EXAMPLE 3

In this example a viscosity of 2800 mPa/s was measured at 20° C., which dropped to 50 mPa/s at 40° C. The permanent shaping agent, whose melting range is between 37° and 40° C., is thus suitable for treatment with the application of heat by radiation or by blowing heated air against it.

EXAMPLE 4

In this example, whose formula was developed especially for dyed hair, the initial viscosity at 20° C. is 2600 mPa/s, at 30° C. it is 900 mPa/s, and at 40° C. it is less than 5 mPa/s. The fusion range of about 30° to 33° C. suggests an additional application of heat in the treatment.

What is claimed is:

1. A composition for permanent shaping of human hair which comprises one or more hair keratin-reducing active substances and at least one viscosity modifying agent compatible therewith, said agent being present in an amount sufficient to impart to said composition at room temperature, an initial viscosity of at least 100 mPa/s and to impart thereto a lowered viscosity, at temperatures in the range 25°–42° C., of below about 50 mPa/s.

2. The permanent shaping composition of claim 1, wherein said viscosity modifying agent is at least one of the group consisting of paraffins, petrolatums, ceresins, fatty alcohols, fatty acids, waxes, polyglycols, polyglycol esters, polyglycol ethers, aminoxides, lanolin derivatives and/or esters and ethers of monovalent or polyvalent organic acids with monovalent or polyvalent alcohols.

3. A method for the permanent shaping of human hair, in which the hair rolled in portions on curlers is treated with a hair-keratin-reducing permanent shaping agent containing a stiffening additive or additives, which at room temperature (20°C.) has a viscosity of at least 100 mPa.s and which, after a sufficient time of action, is rinsed from the hair and the hair is then treated with solution having an oxidizing action, wherein only one permanent shaping agent is applied, which agent upon warming to a temperature within a temperature range between 25°) C. and 42° C. displays a decided loss of viscosity of over 60% with respect to the initial viscosity and to a value under 50 mPa.s, said permanent shaping agent being applied only to the hair portions lying on the outside in the curls of the hair curled without said permanent shaping agent, and then the viscosity of the permanent shaping agent is reduced by elevating the temperature in a range between 25° and 42° C. to such an extent that it becomes thinly fluid and penetrates into the curled hair portions and wets them.

4. The method according to claim 3, wherein the body heat of the person whose hair is to be treated is used to raise the temperature of the permanent shaping agent.

5. The method according to claim 3, wherein the temperature increase necessary to lower the viscosity of the permanent shaping agent is produced by thermal radiation or by blowing with heated air.

6. The method in accordance with claim 3, wherein a permanent shaping agent is used, where the viscosity increasing additive is selected from the group consisting of at least one of paraffins, petrolatums, ceresins, fatty alcohols, fatty acids, waxes, polyglycols, polyglycol esters, polyglycol ethers, amine oxides, lanolin derivative and/or esters and ethers of monovalent or polyvalent organic acids with monovalent or polyvalent alcohols and mixtures thereof.

* * * * *